United States Patent
Blomquist (10) Patent No.: US 9,976,551 B2
(45) Date of Patent: May 22, 2018

(54) SYRINGE CHARACTERIZATION

(71) Applicant: Smiths Medical ASD, Inc., Rockland, MA (US)

(72) Inventor: Michael L. Blomquist, Blaine, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 0 days. days.

(21) Appl. No.: 14/443,928

(22) PCT Filed: Dec. 3, 2013

(86) PCT No.: PCT/US2013/072751
§ 371 (c)(1),
(2) Date: May 19, 2015

(87) PCT Pub. No.: WO2014/089008
PCT Pub. Date: Jun. 12, 2014

(65) Prior Publication Data
US 2015/0297832 A1    Oct. 22, 2015

Related U.S. Application Data

(60) Provisional application No. 61/734,595, filed on Dec. 7, 2012.

(51) Int. Cl.
*A61M 5/20* (2006.01)
*F04B 51/00* (2006.01)
(Continued)

(52) U.S. Cl.
CPC ........... *F04B 51/00* (2013.01); *A61M 5/1452* (2013.01); *A61M 5/1456* (2013.01);
(Continued)

(58) Field of Classification Search
CPC ............................ A61M 5/20; A61M 2209/02
See application file for complete search history.

(56) References Cited

U.S. PATENT DOCUMENTS 4,741,732 A   5/1988   Crankshaw
4,767,406 A   8/1988   Wadham
(Continued)

FOREIGN PATENT DOCUMENTS

GB        2350062 A    11/2000
GB        2350062 B     7/2003
(Continued)

OTHER PUBLICATIONS

International Application No. PCT/US2013/072751, filed Dec. 3, 2013, International Search Report, dated Jun. 3, 2014, 4 pages.
(Continued)

*Primary Examiner* — Erika J Villaluna
(74) *Attorney, Agent, or Firm* — Patterson Thuente Pedersen, P.A.

(57) ABSTRACT

A device for syringe characterization can include a syringe pump with a plunger driver, for a syringe configured to contain can a fluid, wherein the syringe includes a barrel and a plunger. The barrel and the plunger therewithin together define a central longitudinal axis of the syringe. The device can also include a barrel outer diameter sensor, and a linear position sensor in a substantially parallel orientation with the central longitudinal axis of the syringe when the syringe is installed in the syringe pump. At least one moveable marker can be in communication with the linear potentiometer, being capable of indicating a location along the linear potentiometer corresponding to a selected location on the barrel of the syringe when the syringe is installed in the syringe pump. The device can further include software for performing calculations that are indicative of syringe characterization, with respect to locations of selected ones of the
(Continued)

at least one moveable marker and a diameter of the barrel that is sensed by the barrel outer diameter sensor.

5 Claims, 3 Drawing Sheets

(51) Int. Cl.
  *A61M 5/145* (2006.01)
  *A61M 5/168* (2006.01)
  *G06F 19/00* (2018.01)

(52) U.S. Cl.
  CPC ...... *A61M 5/1684* (2013.01); *A61M 5/16804* (2013.01); *A61M 5/16831* (2013.01); *A61M 2205/3389* (2013.01); *A61M 2209/02* (2013.01); *G06F 19/3406* (2013.01)

(56) References Cited

U.S. PATENT DOCUMENTS

| | | |
|---|---|---|
| 4,978,335 A | 12/1990 | Arthur |
| 5,140,862 A | 8/1992 | Pappalardo |
| 5,236,416 A | 8/1993 | McDaniel |
| 5,254,096 A | 10/1993 | Rondelet |
| 5,485,408 A | 1/1996 | Blomquist |
| 5,533,981 A | 7/1996 | Mandro |
| 5,545,140 A | 8/1996 | Conero |
| 5,681,285 A | 10/1997 | Ford |
| 5,814,015 A | 9/1998 | Gargano |
| 6,500,151 B1 | 12/2002 | Cobb |
| D479,324 S | 9/2003 | Kowalski |
| 6,626,862 B1 | 9/2003 | Duchon |
| 6,743,202 B2 | 6/2004 | Hirschman |
| 6,790,198 B1 | 9/2004 | White |
| 7,018,361 B2 | 3/2006 | Gillespie |
| 7,041,082 B2 | 5/2006 | Blomquist et al. |
| 7,044,933 B2 | 5/2006 | Vandiver |
| 7,117,041 B2 | 10/2006 | Engleson |
| 7,169,135 B2 | 1/2007 | Duchon |
| 7,232,424 B2 | 6/2007 | Boyne-Aitken |
| 7,422,570 B2 | 9/2008 | Gerlach |
| 7,442,186 B2 | 10/2008 | Blomquist |
| 7,471,994 B2 | 12/2008 | Ford |
| 7,505,869 B2 | 3/2009 | Hartlaub |
| 7,608,060 B2 | 10/2009 | Gillespie |
| 7,625,354 B2 | 12/2009 | Hochman |
| 7,766,863 B2 | 8/2010 | Gillespie |
| 7,823,287 B2 | 11/2010 | Gerlach |
| 8,161,810 B2 | 4/2012 | Cadieux |
| 8,182,461 B2 | 5/2012 | Pope |
| 8,209,060 B2 | 6/2012 | Ledford |
| 8,225,824 B2 | 7/2012 | Eliuk |
| 2001/0034506 A1 | 10/2001 | Hirschman |
| 2003/0078534 A1 | 4/2003 | Hochman |
| 2003/0149402 A1 | 8/2003 | Gerlach |
| 2003/0233069 A1 | 12/2003 | Gillespie |
| 2004/0092885 A1 | 5/2004 | Duchon |
| 2004/0220526 A1 | 11/2004 | Boyne-Aitken |
| 2006/0064053 A1 | 3/2006 | Bollish |
| 2006/0079833 A1* | 4/2006 | Kobayashi .......... A61M 5/1456 604/65 |
| 2006/0097991 A1 | 5/2006 | Hotelling |
| 2006/0167414 A1 | 7/2006 | Scott |
| 2006/0184123 A1 | 8/2006 | Gillespie |
| 2007/0100281 A1 | 5/2007 | Morris |
| 2008/0161753 A1 | 7/2008 | Gillespie |
| 2009/0005730 A1 | 1/2009 | Gerlach |
| 2009/0005736 A1 | 1/2009 | Flachbart |
| 2009/0188311 A1* | 7/2009 | Cadieux .......... A61M 5/14546 73/149 |
| 2009/0234275 A1 | 9/2009 | Jacobson |
| 2009/0270810 A1 | 10/2009 | DeBelser |
| 2010/0256561 A1 | 10/2010 | Gillespie |
| 2011/0047499 A1 | 2/2011 | Mandro |
| 2011/0193788 A1 | 8/2011 | King |
| 2011/0293443 A1 | 12/2011 | Gillespie |
| 2012/0065990 A1 | 3/2012 | Howard |
| 2012/0091813 A1 | 4/2012 | Spurlin |
| 2013/0281965 A1 | 10/2013 | Kamen |
| 2016/0136353 A1 | 5/2016 | Adams |

FOREIGN PATENT DOCUMENTS

| | | |
|---|---|---|
| GB | 2420719 A1 | 6/2006 |
| GB | 2420719 B | 5/2009 |
| JP | 2011-510749 | 4/2011 |
| WO | WO 9611024 | 4/1996 |
| WO | WO 9625963 | 8/1996 |
| WO | WO 9965548 | 12/1999 |
| WO | WO 0174421 | 10/2001 |
| WO | WO 03105930 | 12/2003 |
| WO | WO 2004/052429 A1 | 6/2004 |
| WO | WO 2004096323 A1 | 11/2004 |
| WO | WO 2005004951 A1 | 1/2005 |
| WO | WO2005004952 | 1/2005 |
| WO | WO2006034178 | 3/2006 |
| WO | WO2008153985 A1 | 12/2008 |
| WO | WO 2009/040026 A2 | 4/2009 |
| WO | WO 2009097441 A1 | 8/2009 |
| WO | WO 2010102750 A1 | 9/2010 |
| WO | WO 2012065649 A1 | 5/2012 |

OTHER PUBLICATIONS

International Preliminary Report on Patentability, International Application No. PCT/US2013/072751, dated Jun. 18, 2015, 6 pages.
Extended European Search Report, Application No. 13859917, dated Nov. 23, 2016, 13 pages.
Office Action dated Oct. 12, 2017 for Japanese Application No. 2015-546545, 9 pages.
Office Action dated May 2, 2017 for Japanese Application No. 201380064092.3, 11 pages.
Office Action dated Feb. 27, 2018 for Japanese Application No. 2015-546545, 5 pages.

* cited by examiner

SYRINGE CHARACTERIZATION

RELATED APPLICATION

This application is a National Phase entry of PCT Application No. PCT/US2013/072751, filed Dec. 3, 2013, which application claims the benefit of priority to U.S. Provisional Patent Application No. 61/734,595 filed Dec. 7, 2012, the entireties thereof being incorporated herein by reference thereto.

TECHNICAL FIELD

This disclosure relates generally to medical devices. More particularly, this disclosure relates to devices for, and methods of, syringe characterization.

BACKGROUND

In the field of medication delivery devices including so-called "syringe pumps," typically a pre-filled medication syringe is mechanically driven under microprocessor control to deliver a prescribed amount or dose of a fluid at a controlled rate to a patient through an infusion line fluidly connected to the syringe. Syringe pumps typically include a motor that rotates a leadscrew. The leadscrew in turn activates a plunger driver which forwardly pushes a plunger within a barrel of the syringe. Pushing the plunger forward thus forces the dose of medication outwardly from the syringe, into the infusion line, and to the patient—typically, intravenously. Examples of syringe pumps are disclosed in U.S. Pat. No. 4,978,335 titled "Infusion Pump with Bar Code Input to Computer," U.S. Pat. No. 8,182,461 titled "Syringe Pump Rapid Occlusion Detection System," and U.S. Pat. No. 8,209,060 titled "Updating Syringe Profiles for a Syringe Pump." As used throughout this disclosure, the term "syringe pump" is intended to generally pertain to any device which acts on a syringe to controllably force fluid outwardly therefrom.

Syringe pumps are used to control the delivery of drugs or fluids to a patient that include, but are not limited to: therapeutic agents; nutrients; drugs; medicaments such as antibiotics, blood clotting agents, and analgesics; and other fluids. The devices can be used to introduce the drugs or fluids into patients' bodies utilizing any of several routes such as, for example, intravenously, subcutaneously, arterially, or epidurally.

In use of syringe pumps it may be desirable, or even required in particular circumstances, to characterize a particular syringe that is installed in a particular device, for determination or prediction of an amount of fluid that will be forced outwardly from the syringe per linear unit travel of the plunger. Commonly, syringes are characterized by manufacturers of syringes and/or syringe pumps according to pre-determined criteria, such as outer diameters. This characterization data may be electronically stored in a syringe database loaded into a syringe pump. Thus, determination of an outer diameter of a particular syringe may primarily serve a purpose of limiting or filtering a list of possible syringes from the pump database which have outer diameters that approximate an outer diameter of the particular syringe. However, various means and methods have also been proposed for characterization of syringes while installed in syringe pumps. These known means and methods of characterization, however, have often merely focused on determinations of outer diameters of syringe barrels by way of moveable measurement jaws, clamps, and the like provided on or in the pumps. Other known means and methods have employed conventional rulers or other linearly ruled components coupled to the pumps, with or without such syringe barrel outer diameter sensors. These rudimentary ruled components have typically been provided in substantially parallel orientations along central longitudinal axes of syringes installed in the pumps. In use of such a ruled device, a health care practitioner would, for example, visually inspect the length of the syringe with respect to the ruled component for visually determining a volume or "length" of fluid contained within the syringe, a location of a tip of the plunger within the syringe, a distance of maximum possible linear travel of the plunger tip with the syringe barrel, and/or any other desired parameters. The user would then typically compare such metrics to a list or database of similar parameters of known syringe types, sizes, and brands, etc. However, such ad hoc visual inspection is prone to errors that may arise from, for example, a lack of adequate visual acuity of the user and variability in interpretation and definition of the parameters. Thus, such known devices and methods have not been entirely satisfactory for syringe characterization—and some such devices and methods have even been deemed to be unsafe and unfit for human use. Furthermore, characterization of "unknown" syringes may be problematic or even impossible within an acceptable degree of reliability, accuracy, and repeatability. In this context, "unknown" refers to those syringes that have not been previously characterized or those that are not listed in, for example, an aforementioned database or look-up table.

It would therefore be useful and advantageous to provide devices and methods which provide some degree of reliability, accuracy, and repeatability in syringe characterization, particularly with respect to unknown syringes.

SUMMARY

This disclosure describes novel and inventive devices for, and methods of, syringe characterization.

A device for syringe characterization can include a syringe pump with a plunger driver, for a syringe containing a fluid, wherein the syringe includes a barrel and a plunger. The barrel and the plunger therewithin together define a central longitudinal axis of the syringe. The device can also include a barrel outer diameter sensor, and a linear position sensor in a substantially parallel orientation with the central longitudinal axis of the syringe when the syringe is installed in the syringe pump. At least one moveable marker can be in communication with the linear potentiometer, being capable of indicating a location along the linear potentiometer corresponding to a selected location on the barrel of the syringe when the syringe is installed in the syringe pump. The device can further include software for performing calculations that are indicative of syringe characterization, with respect to locations of selected ones of the at least one moveable marker and a diameter of the barrel that is sensed by the barrel outer diameter sensor.

In another embodiment, a device for syringe characterization can include a syringe pump with a plunger driver, for a syringe containing a fluid, wherein the syringe includes a barrel and a plunger. The barrel and the plunger therewithin together define a central longitudinal axis of the syringe. The device can also include a barrel outer diameter sensor, and a linear position sensor in a substantially parallel orientation with the central longitudinal axis of the syringe when the syringe is installed in the syringe pump. At least one moveable marker can be in communication with the linear potentiometer, being capable of indicating a location along the linear potentiometer corresponding to a selected location on the barrel of the syringe when the syringe is installed in the syringe pump. The device can further include software for performing calculations that are indicative of syringe characterization, with respect to locations of selected ones of the at least one moveable marker and a diameter of the barrel that is sensed by the barrel outer diameter sensor. An electronic input and display component can be provided in a substantially parallel orientation with the central longitudinal axis of the syringe when installed in the syringe pump, with the electronic input and display component being substituted for the linear potentiometer and the at least one moveable marker.

In another embodiment, a device for syringe characterization can include a syringe pump with a plunger driver, for a syringe containing a fluid, wherein the syringe includes a barrel and a plunger. The barrel and the plunger therewithin together define a central longitudinal axis of the syringe. The device can also include a barrel outer diameter sensor, and a linear position sensor in a substantially parallel orientation with the central longitudinal axis of the syringe when the syringe is installed in the syringe pump. At least one moveable marker can be in communication with the linear potentiometer, being capable of indicating a location along the linear potentiometer corresponding to a selected location on the barrel of the syringe when the syringe is installed in the syringe pump. The device can further include software for performing calculations that are indicative of syringe characterization, with respect to locations of selected ones of the at least one moveable marker and a diameter of the barrel that is sensed by the barrel outer diameter sensor. The barrel outer diameter sensor, the at least one moveable marker, and the software together can function to provide syringe characterization for determination of a selected volume of fluid that is delivered from the syringe from a selected linear displacement of the plunger.

A method of syringe characterization can comprise: providing a device for syringe characterization as aforedescribed; instructing a user of the device to engage the barrel outer diameter sensor, with the sensor thereby determining an outer diameter of a barrel of the syringe; calculating an approximate internal diameter of the barrel of the syringe; instructing the user to move a selected one of the at least one moveable marker to a first position corresponding to a particular volume location along the barrel of the syringe; calculating a second position corresponding to another volume location along the barrel of the syringe and instructing the user to move a selected one of the at least one moveable marker to the second position and provide feedback to the device upon completion thereof; calculating an apparent actual wall thickness of the barrel of the syringe; verifying whether the calculated wall thickness of the barrel of the syringe is within acceptable limits, and if the calculated thickness is not within acceptable limits, then returning to instructing the user to move a selected one of the at least one moveable marker to a first position corresponding to a particular volume location along the barrel of the syringe through calculating an apparent actual wall thickness of the barrel of the syringe until the calculated thickness is within acceptable limits, and if the calculated thickness is within acceptable limits, then determining whether accuracy of the thickness calculation needs to be improved; if accuracy of the calculated thickness does not need to be improved, then calculating an inner diameter of the barrel of the syringe and thus an approximate volume of fluid that is deliverable outwardly from the syringe per linear distance advanced by a plunger tip within the barrel of the syringe; if accuracy of the calculated thickness does need to be improved, then grouping any previously calculated thicknesses with a most recently calculated thickness and determining whether the grouping of calculated thicknesses is sufficiently consistent; if the grouping of calculated thicknesses is not sufficiently consistent, then returning to instructing the user to move a selected one of the at least one moveable marker to a first position corresponding to a particular volume location along the barrel of the syringe; if the grouping of calculated thicknesses is sufficiently consistent, then determining whether a required number of calculations have been made; if the required number of calculations have not been made, then returning to instructing the user to move a selected one of the at least one moveable marker to a first position corresponding to a particular volume location along the barrel of the syringe; if the required number of calculations have been made, then returning to calculating an inner diameter of the barrel of the syringe and thus an approximate volume of fluid that is deliverable outwardly from the syringe per linear distance advanced by a plunger tip within the barrel of the syringe if accuracy of the calculated thickness does not need to be improved; and optionally, identifying a zero volume location on the barrel of the syringe, instructing the user to move a selected one of the at least one moveable marker to a location corresponding to the plunger tip in the syringe, and calculating an actual volume of fluid contained within the syringe.

BRIEF DESCRIPTION OF THE DRAWINGS

Devices for, and methods of, syringe characterization are illustrated by way of example and not limitation in the figures of the accompanying drawings in which.

DETAILED DESCRIPTION

Devices and methods described in greater detail by way of examples herein provide determination and communication to a user of selected syringe characterization parameters through novel and inventive uses of linear position sensors and software together with conventional syringe barrel outer diameter sensors. Such functionality can be advantageously provided in relatively compact and ergonomic medical devices as will be described by example herein.

In an example of an embodiment of a device for, and method of, syringe characterization, the aforementioned functionality is achieved by way of a syringe pump that includes an outer diameter syringe barrel sensor and a linear potentiometer as aforementioned. At least one moveable marker is provided in communication with the linear potentiometer. The at least one moveable marker can be moved to a location corresponding to a selected location on the syringe barrel when the syringe is installed in the pump. The pump includes software for performing calculations with respect to locations of the at least one moveable marker and a sensed outer diameter of the syringe barrel, which are indicative of selected syringe parameters. The pump further includes display means for communicating those parameters to a user, and, optionally, a database of a variety of syringes characterized by the selected parameters such as, for example, type, size, and/or brand of syringe.

Figure 1:
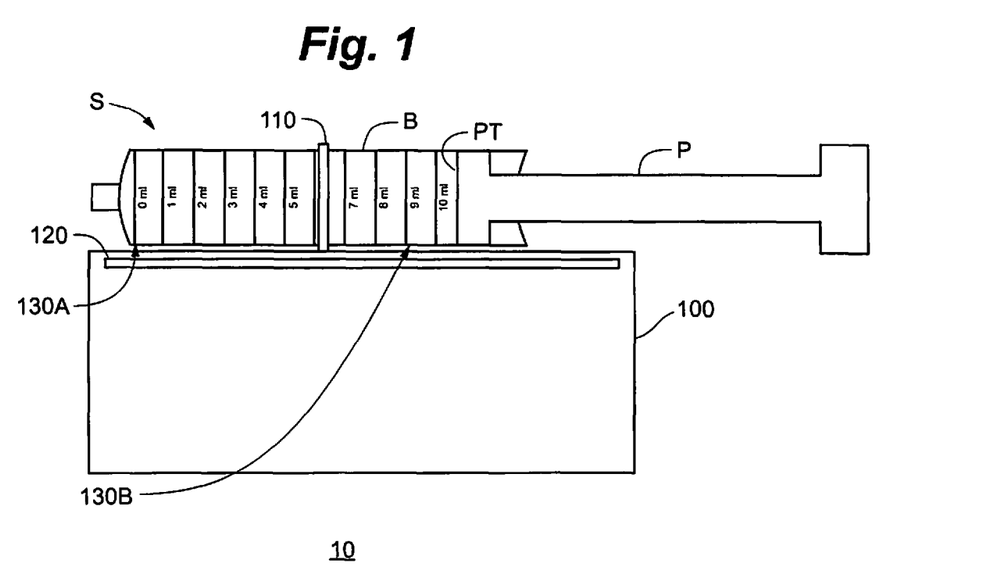
FIG. 1 is a schematic diagram of a device for syringe characterization.

Referring now to FIG. 1, therein illustrated is an example of an embodiment of a device for syringe characterization 10. Device 10 includes a syringe pump 100 for a syringe S having a barrel B and a plunger P with a plunger tip PT. Syringe S is of a size or diameter (N) (e.g., a 30 ml syringe) configured to contain a medication or other fluid to be delivered to a patient from pump 100 acting on syringe S by way of a plunger driver (not illustrated in FIG. 1) as known in the art. Barrel B, and plunger P therewithin, can define a central longitudinal axis of syringe S. Device 10 also includes a syringe barrel outer diameter sensor 110, and a linear position sensor 120 in a substantially parallel orientation with the central longitudinal axis when syringe S is installed in pump 100. Device 10 further includes at least one moveable marker in communication with linear position sensor 120. In the example of FIG. 1, the at least one moveable marker is represented by two individual markers, 130A and 130B, which are slidably coupled to linear position sensor 120 such that they can be moved to desired locations there along. In this regard, the at least one moveable marker is capable of indicating a location along potentiometer 120 corresponding to a selected location on barrel B when syringe S is installed in pump 100 as will be described in operation of device 10. Device 10 also includes software and display means (not depicted in FIG. 1) that can, in an embodiment, be provided by way of suitable computing components and a display screen or graphical user interface within or on pump 100, respectively (not illustrated in FIG. 1) for performing calculations with respect to locations of the at least one moveable marker and communicating those calculations to a user. In general, therefore, it is to be understood that the at least one moveable marker, together with the linear position sensor and the software, enable determination of specific locations—and also measurement of distances between selected points—along the barrel of a syringe. The software can also contain a database of a variety of syringes characterized by selected parameters such as, for example, type, size, and brand as aforementioned, which could then in turn be communicated to the user by the software and display means.

Figure 2:
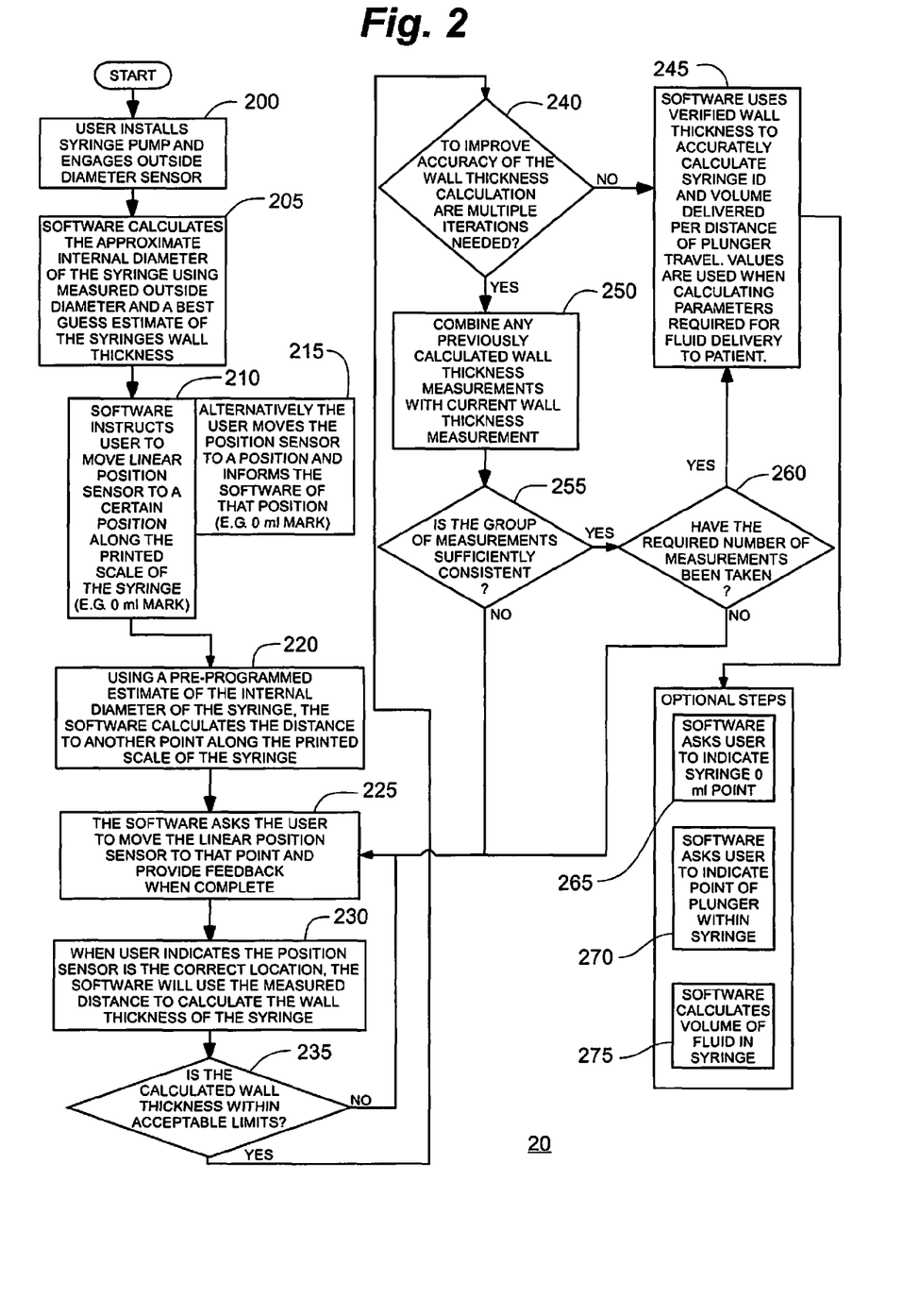
FIG. 2 is a schematic flow or process diagram of a method for syringe characterization.

Referring now to FIG. 2, and with continued reference to FIG. 1, therein illustrated is an example of an embodiment of a method of syringe characterization 20—wherein parenthetical reference numerals herein correspond to the example of a method shown in FIG. 2. In this example of method 20, device 10 as aforedescribed is provided and a particular syringe S is installed (200) in pump 100. Upon commencing operation of device 10, a user of device 10 is instructed (200) by the aforementioned software and display (which hereinafter may also be simply referred to as "the software"—whether including or excluding the display according to a particular component or embodiment of device 10 and/or method 20) to engage outer diameter sensor 110 with barrel B of syringe S. Sensor 110, in cooperation with the software, determines the outer diameter of barrel B of syringe S (205). The software then calculates or predicts an approximate internal diameter of barrel B of syringe S using the outer diameter so determined by sensor 110 and an estimate of a wall thickness of barrel B based upon typical barrel wall thicknesses of typical syringes (205). The software then instructs the user (210) to move a selected one of the at least one moveable marker (e.g., in FIG. 1, 130A or 130B) to a first position along position sensor 120 corresponding to a particular syringe volume location along barrel B of syringe S. In some embodiments, this can be with reference to a printed scale on barrel B corresponding to a zero volume location on barrel B and/or to a point where plunger tip PT could not further advance within syringe S (215). Using the previously calculated or predicted approximate internal diameter of barrel B of syringe S, the software then calculates or predicts (220) a second position along the printed scale of barrel B corresponding to another volume location of syringe S to which it would be possible to move a selected one of the at least one moveable marker. The software then instructs the user to move that selected moveable marker to the second position along the linear position sensor corresponding to the scale of syringe S, and provide feedback to device 10 when that has been completed (225) by way of, e.g., the software and display means. When the user has so indicated that the position of the at least one moveable marker is at the second position, the software then uses a distance measured between the first and second positions to calculate the apparent actual wall thickness of barrel B of syringe S (230). The software can then ask the user, or alternatively make a comparison to an associated database or other internal process, to verify whether the calculated wall thickness of barrel B is within acceptable limits (235). If the calculated wall thickness is not within acceptable limits ("No" in FIG. 2) then the method would return to the aforementioned (225)-(235) until the calculated wall thickness is within acceptable limits. Although not illustrated, a determination of whether the calculated wall thickness is within acceptable limits can be made by the user via user input to the software of device 10 and/or automatically by the software itself, depending upon a particular embodiment of a method of syringe characterization as described by example or otherwise contemplated herein. If the calculated wall thickness is within acceptable limits ("Yes" in FIG. 2) then a determination is made whether accuracy of the wall thickness calculation needs to be improved (240)—again, by the user and/or the software. If accuracy of the wall thickness calculation does not need to be improved ("No" in FIG. 2) then the software uses the barrel B wall thickness so verified to calculate an inner diameter of barrel B and thus an approximate volume of fluid that is deliverable outwardly from syringe S per linear distance advanced by plunger tip PT within barrel B (245) in use of device 10 during delivery of fluid to a patient. In this regard, it is to be noted that for a typical syringe barrel of a cylindrical cross-section, a volume of fluid within the barrel can be calculated as being the product of pi multiplied by the radius of the barrel, squared, and then multiplied by a "length" of the fluid within the barrel (or, $V=\Pi r^2 l$). The "length" of the fluid within the barrel can be represented by a distance measured from a tip of the plunger in the barrel containing the fluid, to a point in the syringe where the plunger tip could not be further advanced. Since the radius of a cylinder is equal to half of its diameter, the volume could also be calculated as the product of pi multiplied by the diameter of the barrel, squared, then multiplied by the length of the barrel, divided by four (or, $V=\Pi d^2 l/4$).

Referring again to (240) in FIG. 2, if however the accuracy of the wall thickness calculation does need to be improved ("Yes" in FIG. 2) then any previous wall thickness calculations are grouped by the software with a most recent wall thickness calculation (250) and a determination is then made—again, by the user and/or the software—of whether the group of wall thickness calculations is sufficiently consistent (255). If the group of wall thickness calculations is not sufficiently consistent ("No" in FIG. 2) then the method returns to (225); but if the group of wall thickness calculations is sufficiently consistent ("Yes" in FIG. 2) then a determination is made of whether a required number of measurements or calculations have been made—again, by the user and/or the software (260). If the required number of measurements or calculations have not been made ("No" in FIG. 2) then the method again returns to (225); but if the required number of measurements or calculations have been made ("Yes" in FIG. 2) then the method proceeds to the aforementioned (245).

With further reference to FIG. 2, the software and display means can optionally instruct the user to indicate a zero volume location on barrel B of syringe S (265) and/or the software can itself extrapolate the zero volume location from measurements and calculations of preceding (200)-(260). The software can then instruct the user (270) to move the at least one moveable marker to a location corresponding to plunger tip PT of syringe S. The software can then calculate (275) an actual volume of the fluid contained within that syringe S.

Although not illustrated, a drive arm in the pump—which acts to advance the plunger in use of the pump—can include a position sensor to sense a present position of the drive arm. With a position of the drive arm thus known and the location of the plunger tip determined as aforementioned, the software can then calculate the length of the plunger arm.

Furthermore, although not illustrated, the software can also compare the aforedescribed characteristics of syringe S (e.g., outer diameter, inner diameter, volume of fluid that is deliverable per linear distance advanced by plunger tip PT, etc.) to a database of previously characterized and known syringes, and through the display means communicate to the user any correspondence between syringe S and a known syringe in the database.

Additionally, although not illustrated, a device and method of syringe characterization can also be utilized for quality control verification and patient safety with known syringes. A known syringe can be installed in a device 10 and the method of syringe characterization as aforedescribed can be performed to verify an expected syringe brand and size. If the displayed syringe characterization parameters do not match with what was expected by the user, then the user can have an indication that the particular syringe is non-conforming or non-standard and should not be used.

Figure 3:
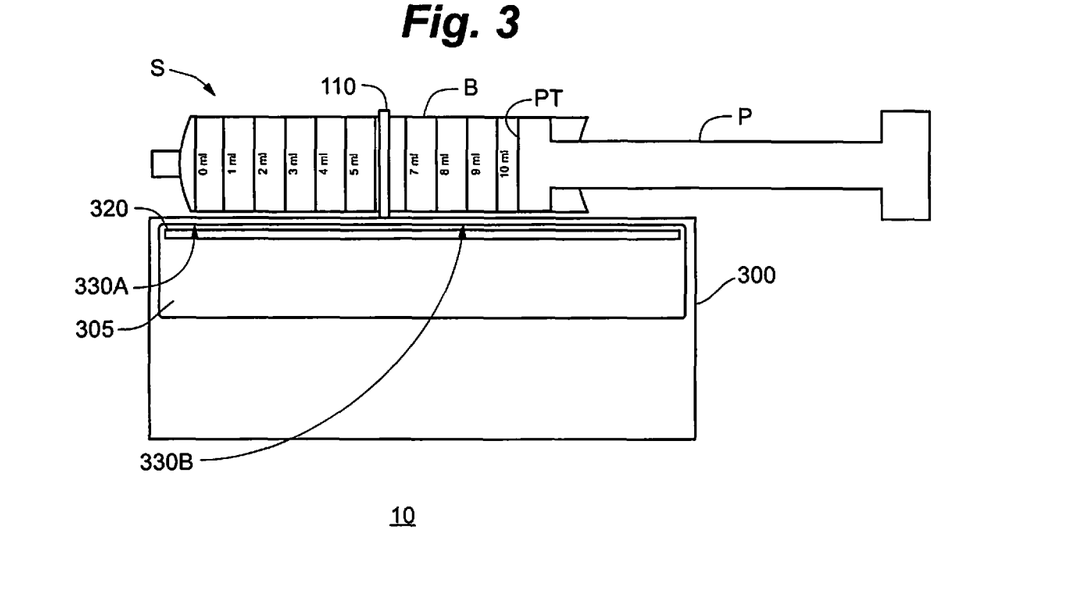
FIG. 3 is a schematic diagram of another embodiment of a device for syringe characterization.

It is to be appreciated and understood, although not illustrated, that suitable push-buttons can be provided with the at least one moveable marker to enable a user to more positively confirm locations associated therewith. In another embodiment, with reference to FIG. 3, an electronic input and display component 305 can be provided in a substantially parallel orientation with the central longitudinal axis of the syringe S when installed in the syringe pump 300. In such an embodiment, the electronic input and display component 305 can be substituted for the linear potentiometer and the at least one moveable marker. For a given display component, the pitch of the rows and/or columns is known by the software. The software can determine the number of rows and/or columns between indicators 330A and 330B on the display 305 or from an edge of the display and from that calculate a position of a marker and/or a distance between two markers or distances between three or more markers. The display and user interface of the device thus can perform the function of one or more linear position sensors 320. Furthermore, the electronic input and display component can comprise, for example, suitable touch screen or LCD technology. Examples of touch screen devices generally are disclosed in U.S. Pat. Applic. Pub. Nos. 2006/0097991 titled "Multipoint Touchscreen" and in 2011/0193788 titled "Graphical Objects that Respond to Touch or Motion Input." Examples of novel and inventive infusion pump technologies employing touch screen devices are disclosed in U.S. Pat. No. 5,485,408 titled "Pump Simulation Apparatus" and in U.S. Pat. Applic. Pub. No. 2009/0270810 titled "Security Features for a Medical Infusion Pump." Thus, for example, a user can mark and measure distances along the syringe, on screen 305, in performance of a method of syringe characterization as described by example or otherwise contemplated herein. Additionally or alternatively a user can move graphical icons—including representations of all or part of a scale on a syringe barrel—on screen, or zoom in or out or otherwise scale a screen image of the syringe, in performance of the method.

It is also to be appreciated and understood that types, components, dimensions, fabrication processes, and other particulars and parameters of aforedescribed example embodiments can be substituted for others as desired, or that accessories can be added thereto. For example, a syringe barrel outer diameter sensor can comprise a "syringe size sensor" that is commercially available in a Medfusion® 3500 Series infusion pump from Smiths Medical ASD, Inc. In that device, the position sensor is a precision potentiometer that produces a voltage (resistance) which is, in turn, proportional to an outside diameter of a barrel of a syringe that is installed in the pump. Generally, however, a linear position sensor can comprise any suitable and/or commercially available sensor (being resistive, capacitive, inductive, or of another type) having an ability to measure an absolute or relative distance along the sensor's axis; and a moveable marker could comprise a corresponding movable portion of the sensor.

Irrespective of a particular embodiment, it is to be appreciated and understood that in embodiments of a device and method of syringe characterization—as disclosed by example or otherwise contemplated herein—the syringe barrel outer diameter sensor, the at least one moveable marker communicating with a linear position sensor, and the software together function to provide syringe characterization for determination of a selected volume of fluid that is delivered from the syringe from a selected linear displacement of the syringe's plunger. In this regard, it is to be particularly appreciated and understood that the novel and inventive devices for and methods of calculating or predicting inner diameters of syringe barrels, as aforedescribed, enable such characterizations of unknown syringes as also aforedescribed. Thus, devices and methods of syringe characterization that have been described by example or otherwise contemplated herein, for syringes that might have been previously unknown, can advantageously enhance accuracy—and thus safety and efficacy—in fluid delivery to patients.

Regardless of particular components or modes of action, it is to be appreciated and understood that devices for, and methods of, syringe characterization such as have been described by example or otherwise contemplated herein, can be able, for a particular linear displacement or travel of a particular plunger, to determine with increased accuracy how much fluid is ultimately delivered. For example, for a particular syringe one millimeter (1 mm) of plunger travel could result in ten milliliters (10 ml) of fluid delivered to the patient.

While devices for, and methods of, syringe characterization have been particularly shown and described with reference to the accompanying figures and specification, it should be understood however that other modifications thereto are of course possible; and all of them are intended to be within the true spirit and scope of novel and inventive devices and methods described herein. Thus, configurations and designs of various features could be modified or altered depending upon particular embodiments. For example, sequencing of various method steps described by example or otherwise contemplated herein could be re-ordered as may be desired in a particular embodiment.

It is also to be understood that dimensioning and scaling of the drawings herein have been chosen to clearly show details of example embodiments. Thus, in some embodiments it is possible that spacing between, or orientations of, various features might be variable and visually different from those illustrated. In any event, dimensioning and scaling could vary significantly across various embodiments of syringe characterization devices and methods.

It is also to be understood in general that any suitable alternatives may be employed to provide novel and inventive devices for, and methods of, syringe characterization described by example or otherwise contemplated herein.

Lastly, compositions, sizes, and strengths of various aforementioned components of devices for, and methods of, syringe characterization described by example or otherwise contemplated herein are all a matter of design choice depending upon intended uses thereof.

Accordingly, these and other various changes or modifications in form and detail may also be made, without departing from the true spirit and scope of devices for, and methods of, syringe characterization that may be defined by the appended claims.

What is claimed is:

1. A device for syringe characterization, comprising:
a syringe pump with a plunger driver, for a syringe configured to contain a fluid, wherein the syringe includes a barrel and a plunger, the barrel and the plunger therewithin together defining a central longitudinal axis of the syringe;
a barrel outer diameter sensor;
a linear position sensor in a substantially parallel orientation with the central longitudinal axis of the syringe when the syringe is installed in the syringe pump;
at least one moveable marker slidably coupled to the linear position sensor to indicate a location along the linear position sensor corresponding to a selected location on the barrel of the syringe when the syringe is installed in the syringe pump; and
software configured to (i) determine a first wall thickness of the syringe based on a sensed barrel outer diameter, (ii) determine a second wall thickness of the syringe based on the indicated location along the linear position sensor corresponding to the selected location on the barrel of the syringe, and (iii) compare the first and second wall thickness to determine if the determined wall thicknesses are within an acceptable limit, before determining a volume of medicament deliverable per distance of plunger travel.

2. The device for syringe characterization of claim 1, wherein an electronic input and display component is provided in a substantially parallel orientation with the central longitudinal axis of the syringe when installed in the syringe pump, with the electronic input and display component being substituted for the linear position sensor and the at least one moveable marker.

3. The device for syringe characterization of claim 1, wherein the barrel outer diameter sensor, the at least one moveable marker, and the software together function to provide syringe characterization for determination of a selected volume of fluid that is delivered from the syringe from a selected linear displacement of the plunger.

4. A method of syringe characterization, comprising:
providing a device for syringe characterization, the device comprising:
a syringe pump with a plunger driver, for a syringe configured to contain a fluid, wherein the syringe includes a barrel and a plunger, the barrel and the plunger therewithin together defining a central longitudinal axis of the syringe;
a barrel outer diameter sensor;
a linear position sensor in a substantially parallel orientation with the central longitudinal axis of the syringe when the syringe is installed in the syringe pump;
at least one moveable marker in communication with the linear position sensor, being capable of indicating a location along the linear position sensor corresponding to a selected location on the barrel of the syringe when the syringe is installed in the syringe pump; and
software for performing calculations that are indicative of syringe characterization, with respect to locations of selected ones of the at least one moveable marker and a diameter of the barrel that is sensed by the barrel outer diameter sensor;
instructing a user of the device to engage the barrel outer diameter sensor, with the sensor thereby determining an outer diameter of a barrel of the syringe;
calculating an approximate internal diameter of the barrel of the syringe;
instructing the user to move a selected one of the at least one moveable marker to a first position corresponding to a particular volume location along the barrel of the syringe;
calculating a second position corresponding to another volume location along the barrel of the syringe and instructing the user to move a selected one of the at least one moveable marker to the second position and provide feedback to the device upon completion thereof;
calculating an apparent actual wall thickness of the barrel of the syringe;
verifying whether the calculated wall thickness of the barrel of the syringe is within acceptable limits, and
if the calculated thickness is not within acceptable limits, then returning to instructing the user to move a selected one of the at least one moveable marker to a first position corresponding to a particular volume location along the barrel of the syringe through calculating an apparent actual wall thickness of the barrel of the syringe until the calculated thickness is within acceptable limits, and
if the calculated thickness is within acceptable limits, then determining whether accuracy of the thickness calculation needs to be improved;
if accuracy of the calculated thickness does not need to be improved, then calculating an inner diameter of the barrel of the syringe and thus an approximate volume of fluid that is deliverable outwardly from the syringe per linear distance advanced by a plunger tip within the barrel of the syringe;
if accuracy of the calculated thickness does need to be improved, then grouping any previously calculated thicknesses with a most recently calculated thickness and determining whether the grouping of calculated thicknesses is sufficiently consistent;
if the grouping of calculated thicknesses is not sufficiently consistent, then returning to instructing the user to move a selected one of the at least one moveable marker to a first position corresponding to a particular volume location along the barrel of the syringe;

if the grouping of calculated thicknesses is sufficiently consistent, then determining whether a required number of calculations have been made;

if the required number of calculations have not been made, then returning to instructing the user to move a selected one of the at least one moveable marker to a first position corresponding to a particular volume location along the barrel of the syringe;

if the required number of calculations have been made, then returning to calculating an inner diameter of the barrel of the syringe and thus an approximate volume of fluid that is deliverable outwardly from the syringe per linear distance advanced by a plunger tip within the barrel of the syringe if accuracy of the calculated thickness does not need to be improved; and optionally, identifying a zero volume location on the barrel of the syringe, instructing the user to move a selected one of said at least one moveable marker to a location corresponding to the plunger tip in the syringe, and calculating an actual volume of fluid contained within the syringe.

5. A syringe pump configured to accept a variety of syringes of different sizes and, upon installation of a syringe, calculate a volume of medicament deliverable per distance of plunger travel based on a sensed size of the syringe, the syringe pump comprising:

a sensor configured to sense an outer diameter of the syringe;

a moveable marker in communication with a linear position sensor configured to sense a selected location along a longitudinal axis of the syringe; and a processor configured to (i) determine a first wall thickness of the syringe based on the sensed outer diameter of the syringe, (ii) determine a second wall thickness of the syringe based on the sensed location along the longitudinal axis of the syringe, and (iii) compare the first and second wall thickness to determine if the determined wall thicknesses are within an acceptable limit, before determining a volume of medicament deliverable per distance of plunger travel.

* * * * *